(12) United States Patent
Palmer (10) Patent No.: US 7,329,839 B2
(45) Date of Patent: Feb. 12, 2008

(54) COVER FOR A CANDLE WARMER

(76) Inventor: Jeffery W. Palmer, 1460 N. 1600 West, Mapleton, UT (US) 84664

( * ) Notice: Subject to any disclaimer, the term of this patent is extended or adjusted under 35 U.S.C. 154(b) by 152 days.

(21) Appl. No.: 11/113,684

(22) Filed: Apr. 25, 2005

(65) Prior Publication Data

US 2006/0240371 A1 Oct. 26, 2006

(51) Int. Cl.
*F27D 11/00* (2006.01)
*A61L 9/00* (2006.01)
*F23D 3/16* (2006.01)

(52) U.S. Cl. .................. 219/438; 392/386; 431/289

(58) Field of Classification Search ........ 219/401–409, 219/438–442; 392/386–393; 431/288–297; D26/9–23
See application file for complete search history.

(56) References Cited

U.S. PATENT DOCUMENTS

| D66,692 S | 2/1925 | Lavell |
| D66,775 S | 3/1925 | Lavell |
| D83,209 S | 2/1931 | Pedersen |
| D150,000 S | 6/1948 | Cohen |
| 5,651,942 A | 7/1997 | Christensen |
| D410,756 S | 6/1999 | Kleinberg |
| 6,627,857 B1 | 9/2003 | Tanner et al. |
| 7,133,605 B2 * | 11/2006 | Niemeyer .................. 392/390 |
| 2003/0209533 A1 | 11/2003 | Tanner et al. |

FOREIGN PATENT DOCUMENTS

| GB | 1547711 | 6/1979 |
| WO | WO 02/100449 A1 | 12/2002 |

OTHER PUBLICATIONS

"Velamour Covers." <http://www.velamour.com/s_other.php> p. 1-2.
"Candle Warmers.com." <http://candlewarmers.com> p. 1.

* cited by examiner

*Primary Examiner*—Sang Paik
(74) *Attorney, Agent, or Firm*—Morriss O'Bryant Compagni, P.C.

(57) ABSTRACT

An apparatus for a candle warming device is disclosed for providing a decorative covering over the candle warming device and for supporting a wax-filled glass candle placed upon a candle warmer. The cover includes a perimeter wall having a base portion defining a first interior surface contour that is generally of the shape of an outer perimeter of a candle warming device. An upper portion is interconnected to the base portion and defines a second interior surface contour that is generally the shape of an outer perimeter of a candle.

23 Claims, 6 Drawing Sheets

COVER FOR A CANDLE WARMER

BACKGROUND OF THE INVENTION

1. Field of the Invention

The present invention relates generally to candle warmers used to heat and melt the wax of a jar-based candle and, more particularly, to a cover for such candle warmers that provides a decorative element to the candle warmer while providing stability between the candle warmer and the candle.

2. State of the Art

Scented candles contained in glass jars are popular in many households. Typically, the wick of the candle is burned to melt the wax of the candle and thus allow a scent contained in the wax to be emitted from the candle. Such candles are available in many different scents.

One alternative to actually burning the candle to emit its scented fragrance is to place the candle upon a candle warming device that melts the wax contained in the glass container of the candle. This method of melting the candle has some advantage over traditional burning methods in that there is no exposed flame that could cause a fire. The candle warmers include an electric heating element heat that heats at a temperature that will melt the wax contained in the glass container of the candle without adversely affecting the glass container.

Figure 1:
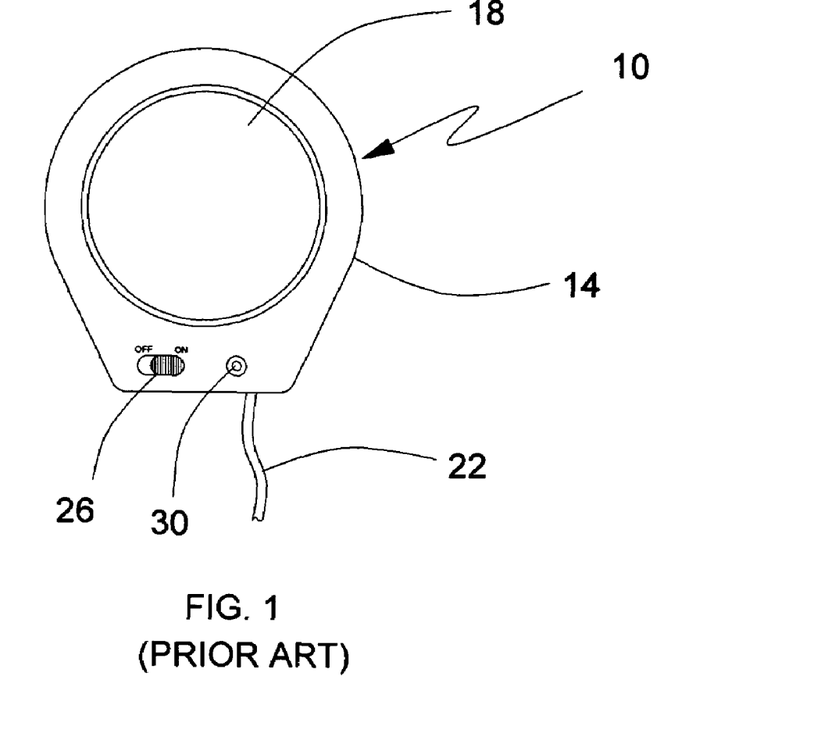
FIG. 1 is a top view of a first prior art candle warming device.
Figure 2:
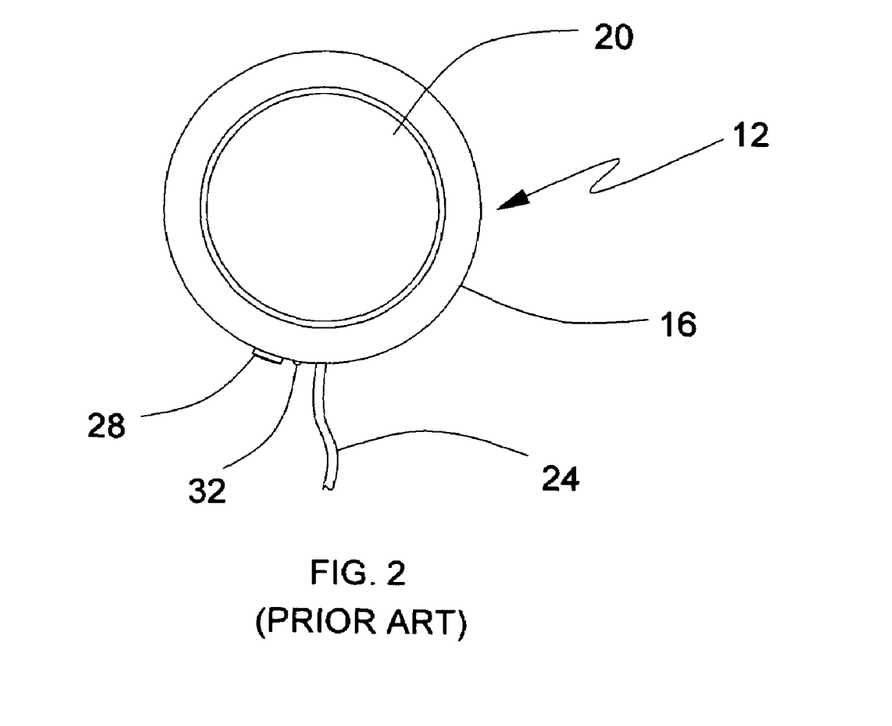
FIG. 2 is a top view of a second prior art candle warming device.

Essentially, such candle warming devices are similar to beverage warmers and come in various shapes and sizes. As shown in FIGS. 1 and 2, prior art candle warming devices 10 and 12 include an exterior housing 14 and 16, respectively, that supports a heated plate surface 18 and 20 that is heated by an internal heating element (not visible). The exterior housing 14 and 16 is typically a very plain, non-ornate structure with a smooth contour. The candle warming devices 10 and 12 are electrical devices that can be powered by household electrical power through cords 22 and 24. The candle warming devices 10 and 12 include power switches 26 and 28, respectively, for turning the warmers 10 and 12 on and off as well as indicator lights 30 and 32, respectively, that illuminate when the warmers 10 and 12 are turned on.

By placing a glass jar based candle upon the plate 18 or 20, and turning the warmer 10 or 12 on, the wax inside the candle will melt from the bottom up until all of the wax contained in the candle has been melted. As the wax melts, the candle will begin to emit its fragrance as if the candle is being burned. As the wax becomes melted, if the candle were to be tipped over, the melted wax could spill from the glass container. Thus, there exists a need in the art to provide a cover for a candle warming device that adds a decorative element to the candle warmer and also supports a candle relative to the candle warming device.

SUMMARY OF THE INVENTION

A cover for a candle warming device is provided for providing a decorative covering over a candle warming device and for supporting a candle placed upon a candle warmer. The cover includes a perimeter wall having a base portion defining a first interior surface contour that is generally of the shape of an outer perimeter of a candle warming device. An upper portion is interconnected to the base portion and defines a second interior surface contour that is generally the shape of an outer perimeter of a candle.

The foregoing characterizing features will become apparent from the following description of certain illustrative embodiments of the invention. The above-described features of the present invention, as well as additional features and advantages, will be set forth or will become more fully apparent in the detailed description that follows and in the appended claims. The novel features which are considered characteristic of this invention are set forth in the attached claims. Furthermore, the features and advantages of the present invention may be learned by the practice of the invention, or will be obvious to one skilled in the art from the description, as set forth hereinafter.

BRIEF DESCRIPTION OF THE DRAWINGS

The following drawings illustrate exemplary embodiments for carrying out the invention. Like reference numerals refer to like parts in different views or embodiments of the present invention in the drawings.

DETAILED DESCRIPTION OF THE ILLUSTRATED EMBODIMENTS

Figure 3:
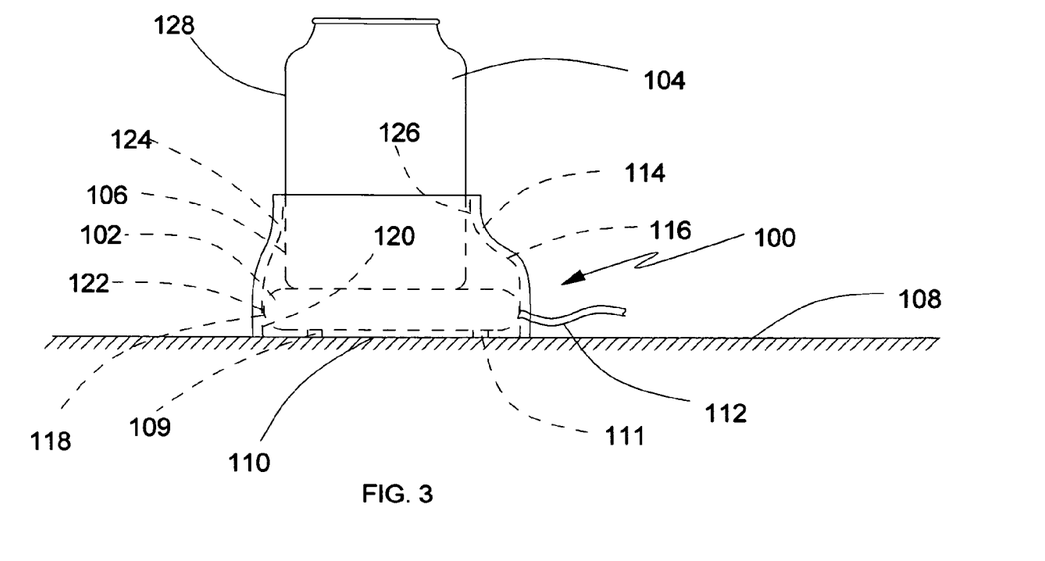
FIG. 3 is side view of a first embodiment of a cover for a candle warming device in accordance with the principles of the present invention.

Referring now to the drawings, FIG. 3 illustrates a cover, generally indicated at 100, that fits over a candle warming device 102 and around a portion of a glass jar-type candle 104. The cover 100 is generally in the form of a "skirt" that surrounds the candle warming device 102 and extends around a portion of the base portion 106 of the candle 104. As illustrated, the cover 100 is configured such that the bottom edge 110 of the cover 100 rests upon a surface 108, such as a table top, countertop, or other stationery surface. Housed within the cover 100 is the candle warming device 102, which also rests upon the surface 108 with feet 109 and 111 that are typically in the form of rubber pads, and a portion 106 of the candle 104. The electrical cord 112 for the candle warming appliance extends through a side wall 114 of the cover 100.

The perimeter wall or sidewall 114 of the cover 100 is provided with an internal contour 116 having a base portion 118 defining a first interior surface contour 120 that is generally the shape of the outer perimeter 122 of the candle warming device 102. The sidewall 114 also has an upper portion 124 interconnected to the base portion 118 defining a second interior surface contour 126 that is generally a shape of an outer perimeter 128 of the candle 104, in this example, cylindrical.

Figure 4:
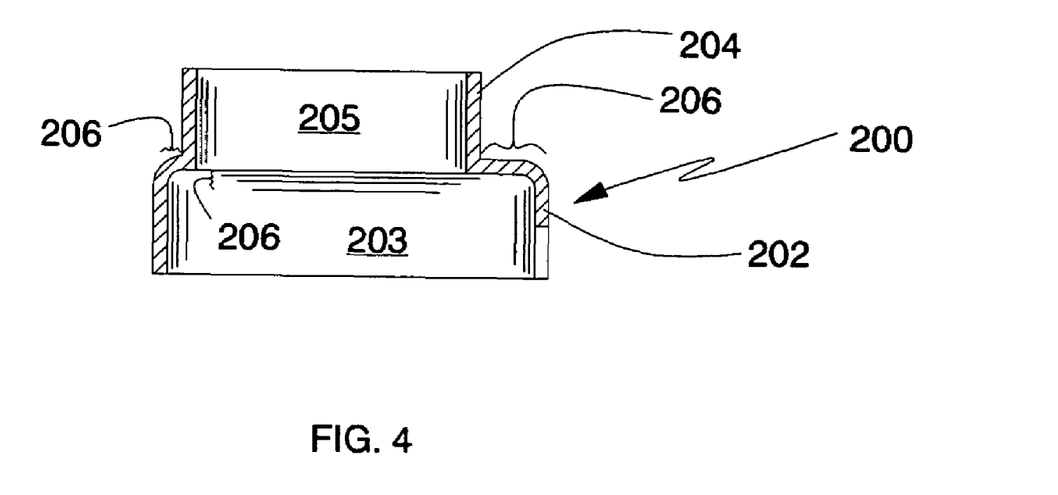
FIG. 4 is a cross-sectional side view of a second embodiment of a cover for a candle warming device in accordance with the principles of the present invention.

Referring now to FIG. 4, there is shown a cross-sectional view of a cover, generally indicated at 200, in accordance with the principles of the present invention. The cover 200 includes a first upwardly extending wall 202 defining a first internal contour 203 configured to substantially match an exterior contour of a candle warming device (such as the candle warming device 102 shown in FIG. 3). The cover 200 also includes a second upwardly extending wall 204 defining a second internal contour 205 configured to substantially match an exterior contour of a candle (such as the candle 104 shown in FIG. 3). The first and second upwardly extending walls 202 and 204, respectively, are interconnected with a transitional interface or portion 206 that extends between the first and second upwardly extending walls 202 and 204, respectively. This transitional interface 206 is shown as being an integral portion of the first and second upwardly extending walls 202 and 204. It is also contemplated, however, that the walls 202 and 204 and/or the transitional interface 206 could be provided in two or more separate components that are connected or attached together. Thus, while the cover 200 is illustrated as being formed from a single integral component, it may also be formed from various members that form the cover.

As illustrated, the effective diameter of the interior surface contour 205 is less than the effective diameter of the interior surface contour 203. The shape of the contour 203 is configured to fit over and around a candle warming appliance (see FIG. 3) in a manner that retains the candle warming device relative to the cover 200 such that the cover 200 can be easily placed over the candle warming device. The shape of the contour 205 is configured to fit around the base portion of a candle (see FIG. 3) that is resting upon the candle warming device. Again, the diameter of the contour 205 is such that the candle is held and retained by the cover 200. Because the cover also holds and maintains the relative position of the candle warming device relative to the cover 200, the candle is maintained in relative position to the candle warmer.

In use, when a candle is placed upon the warming device as is shown in FIG. 3, the wax within the candle is melted from the heat produced by the candle warming device. The candle warming device is essentially a heating plate that generates heat sufficient to melt the wax inside the candle, but low enough to prevent breaking of the glass jar used to hold the candle wax. Initially, the wax adjacent the bottom of the candle where the heat is applied will melt first. Eventually, however, all of the wax within the candle melts. When the melted wax reaches the top of the candle, the fragrances contained in the candle wax are released into the surrounding air. As such, the fragrances in the candle can be enjoyed without having to actually burn a candle in a traditional manner (i.e., with a flame).

Because such candle warming devices require virtually all of the candle wax to be melted in order for the fragrances in the candle wax to be released, if the candle were to be tipped over, a significant portion, if not almost all, of the melted candle wax would be spilled. In addition to the obvious mess that such a spill would create, given the fact that typical candles used with such candle warmers often contain 16 ounces or more of candle wax, because the wax is hot, human contact with the hot wax could cause burns.

The cover 200 prevents the candle from being knocked free from the candle warming device. That is, the upper wall 204 prevents the candle from moving relative to the candle warming device, as may be the case if one inadvertently were to bump the side of the candle.

Figure 5:
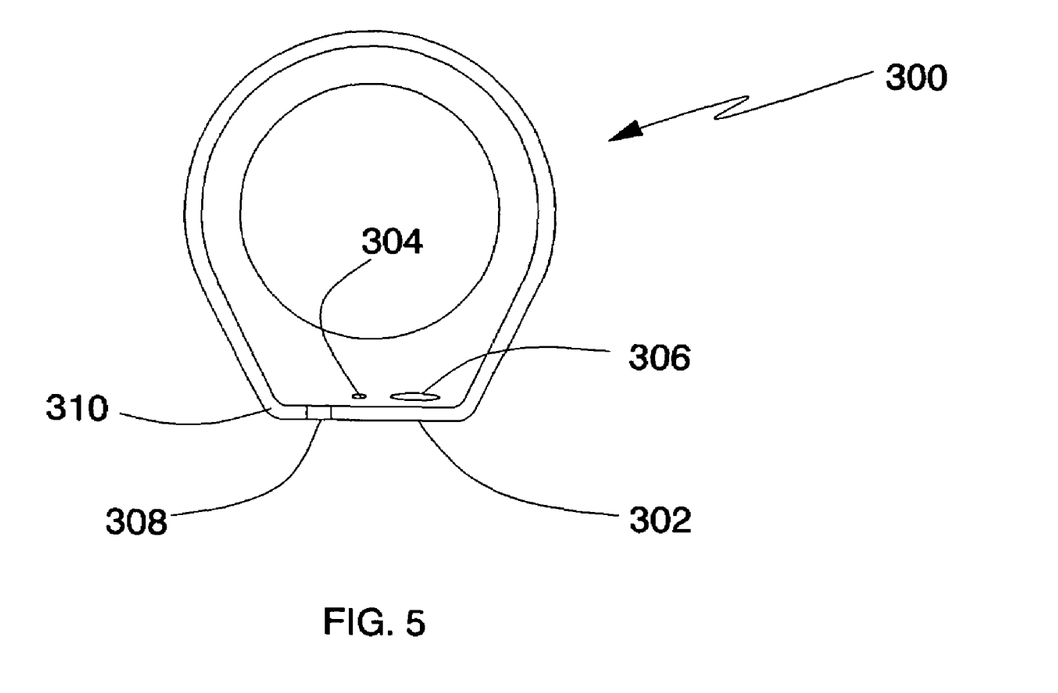
FIG. 5 is a bottom view of a third embodiment of cover for a candle warming device in accordance with the principles of the present invention.
Figure 6:
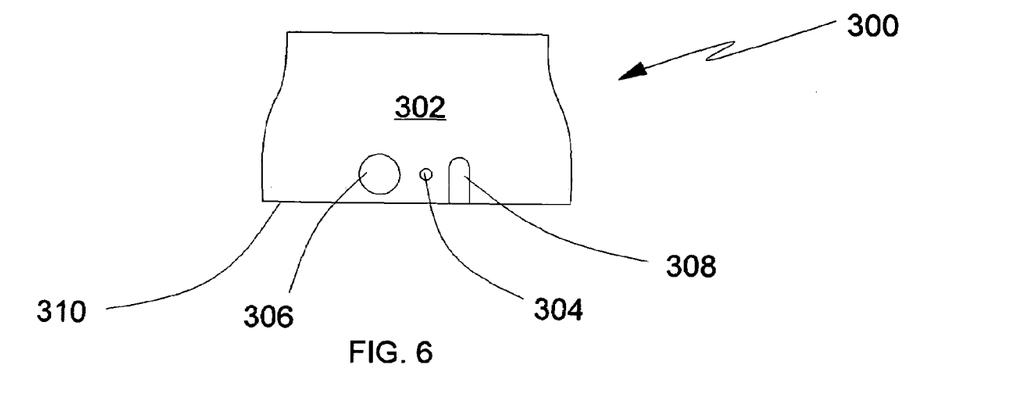
FIG. 6 is a back side view of the cover illustrated in FIG. 5.

As shown in FIGS. 5 and 6, a cover, generally indicated at 300, is illustrated. The cover 300 is similar in configuration to the cover 200 illustrated in FIG. 4. Along one side 302 which would actually represent the back of the cover 300, are first and second apertures 304 and 306 and slot or channel 208. The cannel 308 extends from the bottom edge 310 of the cover 300 is provided to allow passage of an electrical cord (such as the cord 112 shown in FIG. 3) from a candle warming appliance (not shown). In addition, the aperture 306 allows for access to an on/off switch provided on the candle warming appliance. The aperture 308 is provided to allow visualization of an on light through the cover 300.

Figure 7:
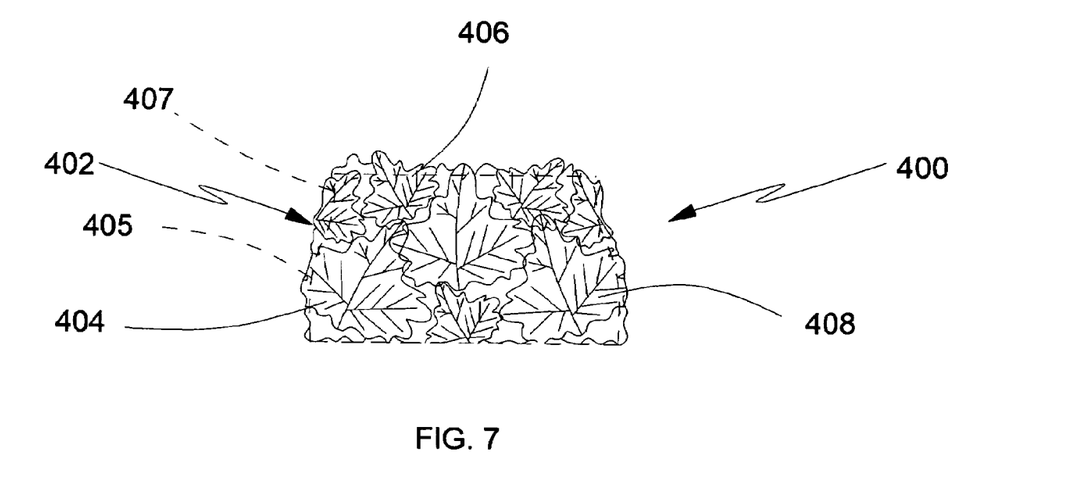
FIG. 7 is a front view of a fourth embodiment of a cover for a candle warming device in accordance with the principles of the present invention.
Figure 8:
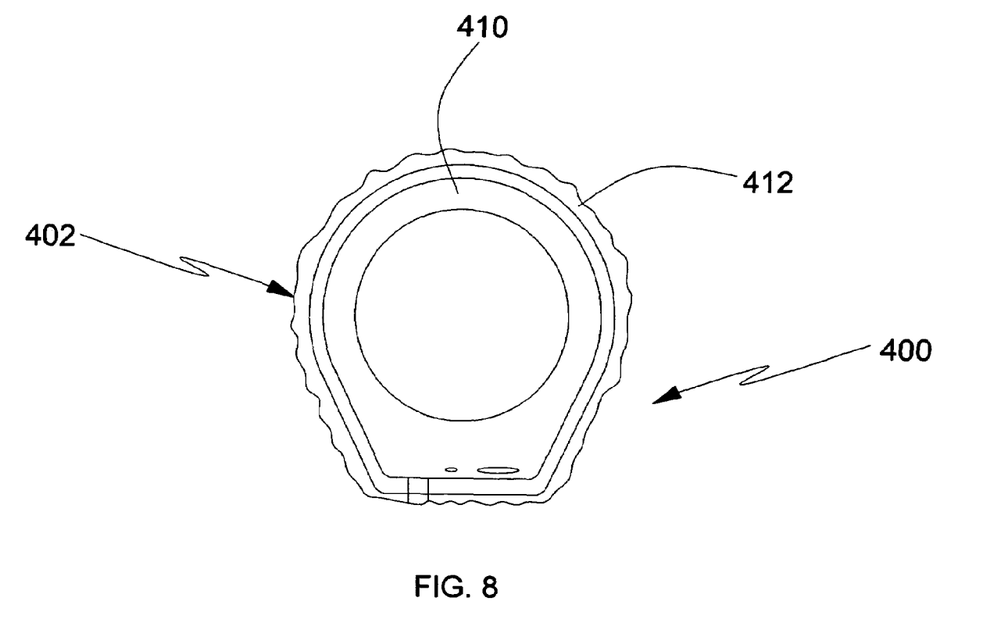
FIG. 8 is a bottom view of the cover illustrated in FIG. 7.

Referring now to FIGS. 7 and 8, another added benefit of a cover, generally indicated at 400, in accordance with the principles of the present invention, is the inclusion of a decorative element, generally indicated at 402 to the exterior surface 404 of the cover 400. The decorative element 402 may be comprised of a plurality of individual decorative elements, such as elements 404, 406 and 408, for example, that are attached to the outer surface of the cover element 410. The decorative elements 404, 406 and 408, may be adhesively attached to the outside surface of the cover element 410 or otherwise bonded thereto by methods known in the art. As such, there is one decorative element 404 attached to a first upwardly extending wall 405 and another decorative element 406 attached to a second upwardly extending wall 407 of the cover element 410.

As such, the cover 400 is essentially a dual layer structure with the cover element 410 forming an internal layer that is used as a form for applying the decorative element 412 thereto. The decorative element 412 forms a second outer layer over the internal cover element 410. Thus, while the exemplary embodiment is shown as having leaf-shaped decorative elements 404, 406 and 408, the decorative elements could be provided in virtually any configuration in order to provide various decorative themes.

Figure 9:
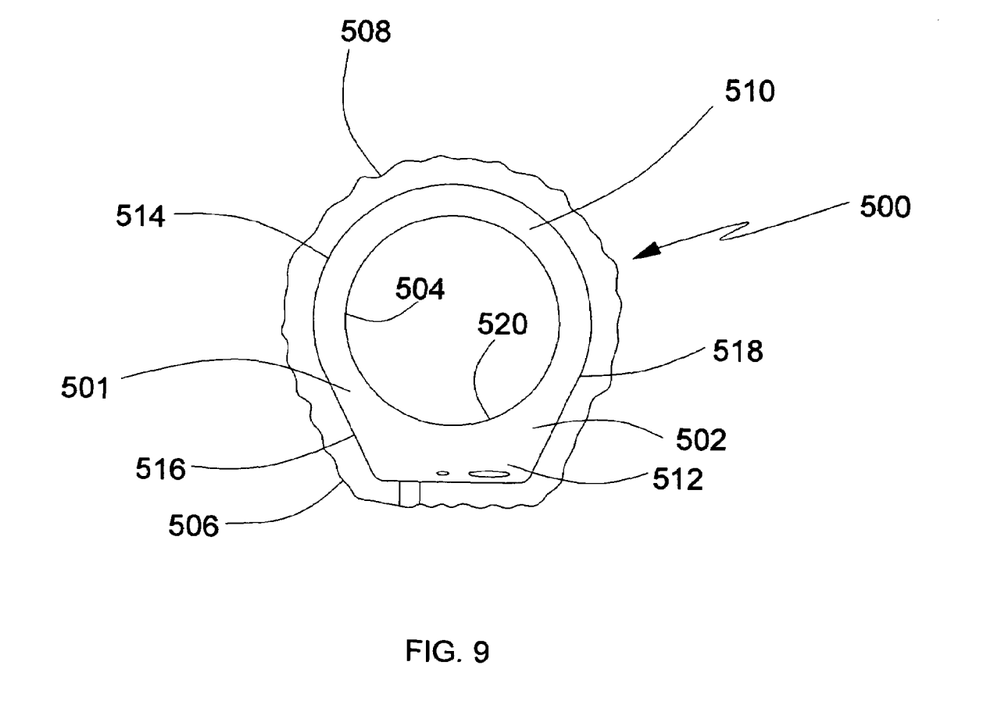
FIG. 9 is a bottom view of a fifth embodiment of a cover for a candle warming device in accordance with the principles of the present invention.

As shown in FIG. 9, a cover, generally indicated at 500, in accordance with the principles of the present invention is formed from a single, integral component. The cover 500 has an inside surface 501 that defines an internal chamber or recess 502 configured for receiving a candle warming device. The internal shape or contour of the recess 502 is of a size and shape that is approximately equal, but slightly larger than an external size and shape of a candle warming appliance.

The inside surface 501 also defines a candle retainer portion 504 for holding at least a base portion of a candle relative to a candle warming appliance. The internal shape or contour of the candle retainer portion 504 is of a size and shape that is approximately equal, but slightly larger than an internal size and shape of a candle.

The cover 500 also includes a decorative outer surface 506 that substantially covers the exterior of the cover 506. The decorative outer surface 506 is integrally formed with the cover 500. That is, the cover 500 is formed from a single integral unit with the decorative outer surface 506 being formed into the exterior 508. Thus, the cover 500 may be molded, as by injection molding plastic, or formed by other molding or machining processes known in the art, whether the cover is formed from plastic, wood, resins, cement or cement-like materials, or the like.

Figure 10:
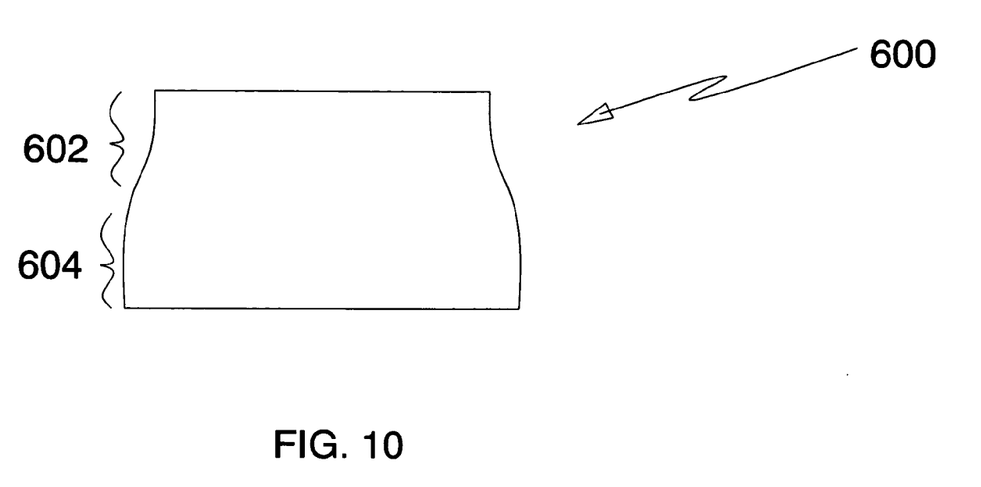
FIG. 10 is a side view of a sixth embodiment of a candle warming device in accordance with the principles of the present invention.

While the cover 500 shown in FIG. 9 is configured to cover a candle warming device, such as the candle warming device shown in FIG. 1, other configurations of candle warming devices exist in the marketplace, such as the candle warming device 12 shown in FIG. 2. That is, the cover 500 has a partial cylindrically shaped portion 510 and a trapezoidally shaped portion 512. As such, as shown in FIG. 10, a cover, generally indicated at 600, is of an overall, generally cylindrical configuration, having a top cylindrical portion 602 configured for fitting around and supporting a candle (not shown) and a bottom cylindrical portion 604 configured for fitting around a circular-shaped candle warming device. Thus, despite the configurations of covers illustrated herein, it is contemplated according to the present invention to provide a cover that is configured to receive one or more types of candle warming devices. For example, the cover 500 shown in FIG. 9 could accommodate a candle warmer 10 shown in FIG. 1 or a candle warmer 12 shown in FIG. 2 with the internal side walls 514, 516 and 518 being able to substantially center the candle warming device 12 relative to the cylindrical opening 520 in order to properly position the candle warming device 12 so that a candle inserted into the opening 520 will properly rest upon the heating element of the candle warmer 12.

It is understood that the terminology used herein is used for the purpose of describing particular embodiments only and is not intended to limit the scope of the present invention. It is also understood that, as used herein and in the appended claims, the singular forms "a," "an," and "the" include plural reference, unless the context clearly dictates otherwise.

Unless defined otherwise, all technical and scientific terms used herein have the same meanings as commonly understood by one of ordinary skill in the art to which this invention belongs. While various methods, compositions, and materials of the present invention are described herein, any methods and materials similar or equivalent to those described herein may by used in the practice or testing of the present invention. All references cited herein are incorporated by reference in their entirety and for all purposes.

While the foregoing advantages of the present invention are manifested in the illustrated embodiments of the invention, a variety of changes can be made to the configuration, design and construction of the invention to achieve those advantages. Hence, reference herein to specific details of the structure and function of the present invention is by way of example only and not by way of limitation.

What is claimed is:

1. A cover for an electrical candle warming device, the candle warming device configured for melting the wax of a glass jar candle having an exterior housing configured for resting on a surface, comprising:
   a first upwardly extending wall defining a first internal contour configured to substantially match an exterior contour of the exterior housing of the candle warming device and defining a first open end for receiving the candle warming device therein;
   a second upwardly extending wall defining a second internal contour configured to substantially match an exterior contour of the glass jar candle, said second upwardly extending wall interconnected to said first upwardly extending wall, said second internal contour defining an effective area that is less than an effective area defined by said first internal contour and defining a second opposing open end for receiving the glass jar candle therein;
   said cover being separate from said candle warming device and readily removable from said candle warming device.

2. The cover of claim 1, further including a transitional interface between said first upwardly extending wall and said second upwardly extending wall.

3. The cover of claim 2, wherein said first upwardly extending wall, said second upwardly extending wall and said transitional interface are continuous and integrally formed.

4. The cover of claim 1, further including at least one decorative element on an outer surface of said first and second upwardly extending walls.

5. The cover of claim 4, wherein said at least one decorative element is integrally formed in said first and second upwardly extending walls.

6. The cover of claim 4, wherein said at least one decorative element is attached to outer surfaces of said first and second upwardly extending walls.

7. The cover of claim 6, wherein said at least one decorative element comprises a plurality of decorative elements adhesively attached to said outer surfaces of said first and second upwardly extending walls.

8. The cover of claim 1, wherein said first upwardly extending wall defines a first aperture for receiving a power cord of the candle warming device therethrough.

9. The cover of claim 8, wherein at least one of said first and second upwardly extending walls defines a second aperture for accessing an on/off switch of the candle warming device therethrough.

10. The cover of claim 1, wherein said first wall has a height sufficient to allow a bottom surface of said first wall to rest upon a support surface when covering the candle warming device.

11. The cover of claim 1, wherein said second wall defines a cylindrically shaped opening for receiving a portion of the candle therein and for supporting the sides of the candle relative to the candle warming device when the candle is placed upon a heating element of the candle warming device.

12. A cover for a candle warming device, comprising:
   a candle warming device having an exterior housing and an electrically heated surface supported by said exterior housing, said candle warming device configured for resting on a surface;
   a glass jar candle;
   a cover comprising: a first upwardly extending wall defining a first internal contour configured to substantially match an exterior contour of the candle warming device, surrounding said exterior housing of said candle warming device and defining a first open end for receiving the candle warming device therein; and
   a second upwardly extending wall defining a second internal contour configured to substantially match an exterior contour of the glass jar candle and defining a second opposing open end for receiving the glass jar candle therein, said second upwardly extending wall interconnected to said first upwardly extending wall, said second internal contour having an effective diameter that is less than an effective diameter of said first internal contour
   said cover being separate from said candle warming device and readily removable from said candle warming device.

13. The cover of claim 12, further including a transitional interface between said first upwardly extending wall and said second upwardly extending wall.

14. The cover of claim 13, wherein said first upwardly extending wall, said second upwardly extending wall and said transitional interface are integrally formed.

15. The cover of claim 12, further including at least one decorative element on an outer surface of said first and second upwardly extending walls.

16. The cover of claim 15, wherein said at least one decorative element is integrally formed in said first and second upwardly extending walls.

17. The cover of claim 15, wherein said at least one decorative element is attached to outer surfaces of said first and second upwardly extending walls.

18. The cover of claim 17, wherein said at least one decorative element comprises a plurality of decorative elements adhesively attached to said outer surfaces of said first and second upwardly extending walls.

19. The cover of claim 12, wherein said first upwardly extending wall defines a first aperture for receiving a power cord of the candle warming device therethrough.

20. The cover of claim 19, wherein at least one of said first and second upwardly extending walls defines a second aperture for accessing an on/off switch of the candle warming device therethrough.

21. The cover of claim 12, wherein said first wall has a height sufficient to allow a bottom surface of said first wall to rest upon a support surface when covering the candle warming device.

22. The cover of claim 12, wherein said second wall defines a cylindrically shaped opening for receiving a portion of the candle therein and for supporting the sides of the candle relative to the candle warming device when the candle is placed upon a heating element of the candle warming device.

23. The cover of claim 1, wherein at least a portion of a bottom edge of said first upwardly extending wall is configured for resting on the surface.

* * * * *